(12) United States Patent
Kraus et al.

(10) Patent No.: US 9,140,676 B2
(45) Date of Patent: Sep. 22, 2015

(54) SMOKE DETECTION SYSTEM AND METHOD FOR OPERATING A SMOKE DETECTION SYSTEM

(71) Applicant: AIRBUS OPERATIONS GMBH, Hamburg (DE)

(72) Inventors: Fabian Kraus, Hamburg (DE); Benjamin Martens, Hamburg (DE)

(73) Assignee: AIRBUS OPERATIONS GMBH, Hamburg (DE)

( * ) Notice: Subject to any disclaimer, the term of this patent is extended or adjusted under 35 U.S.C. 154(b) by 0 days.

(21) Appl. No.: 13/900,208

(22) Filed: May 22, 2013

(65) Prior Publication Data

US 2013/0312488 A1 Nov. 28, 2013

Related U.S. Application Data

(60) Provisional application No. 61/651,022, filed on May 24, 2012.

(30) Foreign Application Priority Data

May 24, 2012 (EP) ..................................... 12004050

(51) Int. Cl.
*G08B 17/10* (2006.01)
*G01N 33/00* (2006.01)
*B64D 45/00* (2006.01)

(52) U.S. Cl.
CPC ............ *G01N 33/0026* (2013.01); *G08B 17/10* (2013.01); *B64D 2045/009* (2013.01)

(58) Field of Classification Search
CPC . G01N 27/407; G08B 17/10; B64D 2045/009
USPC .............................................. 73/23.31, 31.02
See application file for complete search history.

(56) References Cited

U.S. PATENT DOCUMENTS

| | | | |
|---|---|---|---|
| 4,017,733 A * | 4/1977 | Ishii et al. ...................... | 250/381 |
| 4,564,762 A * | 1/1986 | Doherty et al. ............... | 250/381 |
| 5,261,855 A | 11/1993 | Law | |
| 5,625,346 A | 4/1997 | Shim | |
| 6,024,639 A | 2/2000 | Scherer | |
| 6,285,291 B1 * | 9/2001 | Knox et al. .................... | 340/634 |
| 8,224,621 B2 * | 7/2012 | Ajay et al. ..................... | 702/176 |
| 2003/0063007 A1 * | 4/2003 | Seelbach et al. .............. | 340/628 |
| 2004/0246137 A1 | 12/2004 | Bobenhausen | |
| 2005/0178539 A1 * | 8/2005 | Rotta et al. .................... | 165/235 |
| 2006/0267786 A1 | 11/2006 | Freiling | |
| 2012/0074258 A1 * | 3/2012 | Papke et al. ................. | 244/118.5 |

FOREIGN PATENT DOCUMENTS

EP 1 437 701 7/2004

* cited by examiner

*Primary Examiner* — Laura Martin
*Assistant Examiner* — Alex Devito
(74) *Attorney, Agent, or Firm* — Dickinson Wright PLLC

(57) ABSTRACT

A smoke detection system includes at least one smoke detector which is installed in a first partial region of a region to be monitored by way of the smoke detection system. The smoke detection system further includes at least one fluid injection device which is configured to inject a fluid into the region to be monitored by way of the smoke detection system in a direction of at least one smoke detector such that in an emergency case, when smoke is present in a second partial region of the region to be monitored the smoke is transported to the at least one smoke detector.

18 Claims, 3 Drawing Sheets

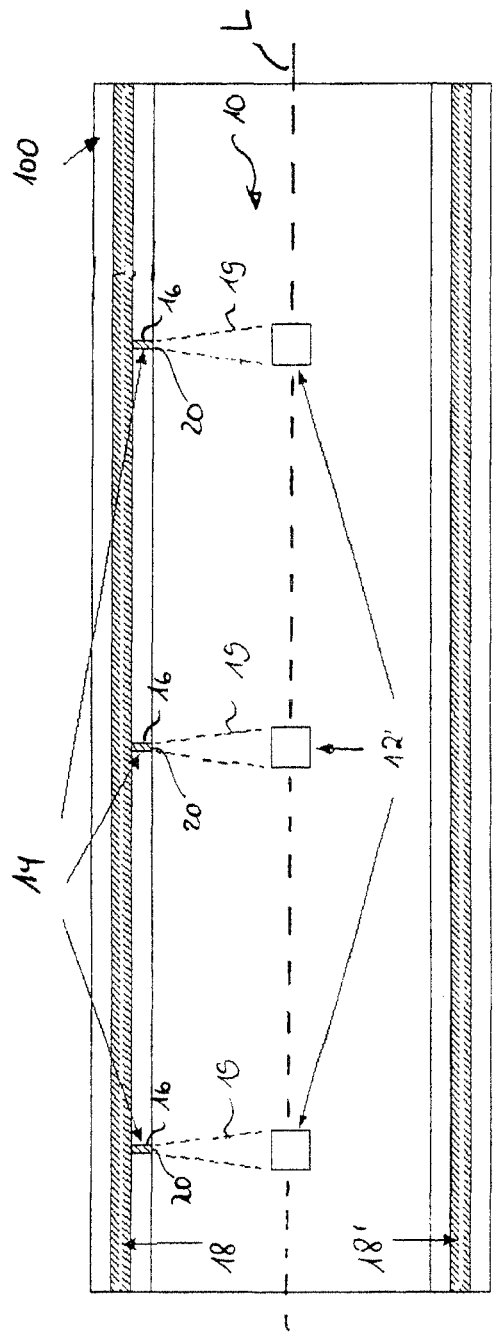

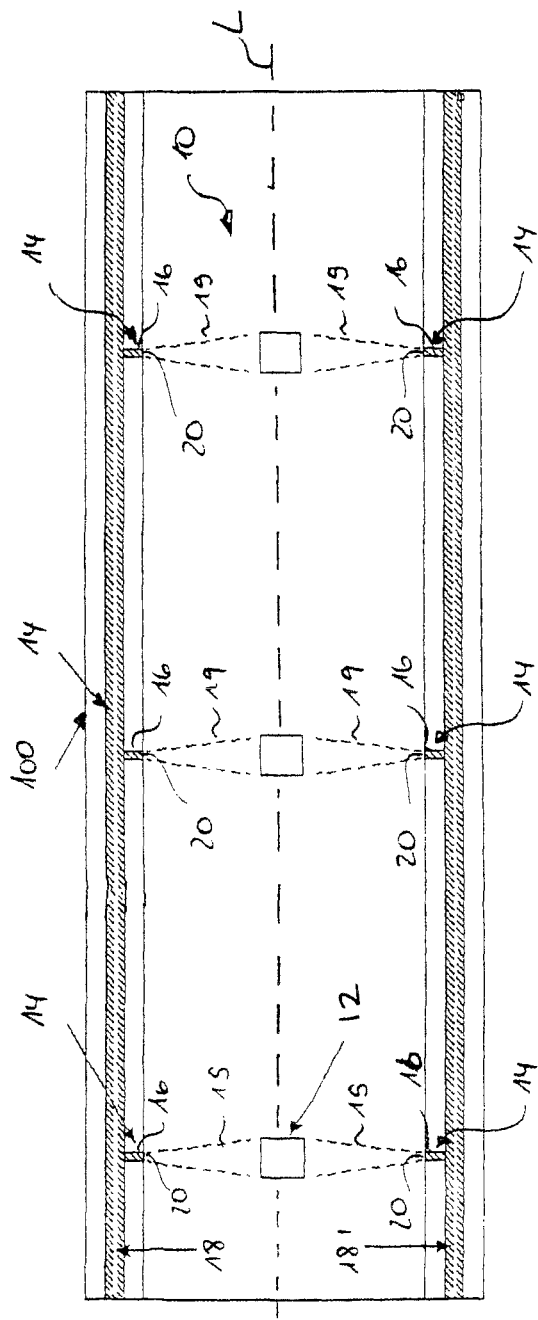

SMOKE DETECTION SYSTEM AND METHOD FOR OPERATING A SMOKE DETECTION SYSTEM

CROSS REFERENCE TO RELATED APPLICATIONS

This application is entitled to and claims the benefit of European Application No. EP 12004050.6 filed May 24, 2012 and U.S. Provisional Application No. 61/651,022, filed May 24, 2012, the disclosures of each of which, including the specification, claims, drawings and abstract, are incorporated herein by reference in their entirety.

FIELD

The invention concerns a smoke detection system and a method for operating a smoke detection system which are particularly suitable for use in the cabin of a vehicle such as an aircraft.

BACKGROUND

The cabin of modern aircraft is equipped with a plurality of smoke detectors which allow a fast and reliable detection of smoke and thus significantly reduce the risk of fire on board the aircraft. Typically, the smoke detectors are installed in a ceiling region of the aircraft cabin. At certain operational states of the aircraft, for example during ground operation of the aircraft at hot ambient temperatures and/or intense solar radiation, the aircraft outer shell is heated while the interior of the aircraft cabin is cooled by means of the aircraft air conditioning system. This may cause the formation of air layers having different temperatures within the aircraft cabin. In particular, due to the injection of cool air conditioned air into the aircraft cabin through air outlets disposed in a sidewall region or a floor region of the aircraft cabin, a layer of cool air may form in a lower region of the aircraft cabin, whereas a layer of warm air may be present in the ceiling region of the aircraft cabin.

A warm air layer prevailing in the ceiling region of the aircraft cabin may hinder or at least delay a rising of smoke, which is generated or present in the lower region of the aircraft cabin, to the ceiling region of the aircraft cabin due to thermal convection. Therefore, additional smoke sensors with corresponding electrical connections have to be provided in the lower region of the aircraft cabin. Alternatively or additionally thereto, suitable ventilation means, for example in the form of fans or blowers, may be used for dissolving undesired air layer structures which may form within the aircraft cabin.

SUMMARY

The invention is directed to the object to provide a smoke detection system and a method for operating a smoke detection system which, in an emergency case, allow a fast and reliable detection of smoke and which are particularly suitable for use in a vehicle such as an aircraft which is operated under various ambient conditions.

This object is addressed by a smoke detection system according to features of attached claims and a method for operating a smoke detection system according to features of attached claims.

A smoke detection system according to the invention comprises at least one smoke detector which is installed in a first partial region of a region to be monitored by means of the smoke detection system. The smoke detector may be a conventional smoke detector. It is, however, also conceivable to employ in the smoke detection system according to the invention an aspirating smoke detector, i.e. a smoke detector which is adapted to generate a suction or intake flow of ambient air to the smoke detector. The region to be monitored by means of the smoke detection system may be a region of a building, such as, for example, a room, but preferably is a region of a vehicle such as an aircraft which is operated under various ambient conditions. For example, the smoke detection system according to the invention may be used to monitor a vehicle cabin or a partial region of a vehicle cabin, in particular an aircraft cabin or a partial region of an aircraft cabin. The first partial region of the region to be monitored may, for example, be a ceiling region. Smoke, which is generated anywhere in the region to be monitored, typically rises to the ceiling region of the region to be monitored due to thermal convection. Therefore, smoke detectors which are installed in the ceiling region of the region to be monitored typically allow a reliable detection of smoke generated at an arbitrary site within the region to be monitored.

The smoke detection system further comprises at least one fluid injection device. The fluid injection device is configured to inject a fluid into the region to be monitored in a direction of the at least one smoke detector such that in an emergency case, when smoke is present in a second partial region of the region to be monitored, the smoke is transported to the at least one smoke detector. The second partial region of the region to be monitored may be a region which is located immediately adjacent to the first partial region or which is located remote from the first partial region. For example, the second partial region of the region to be monitored may be a lower region of the region to be monitored, i.e. a partial region of the region to be monitored which is disposed below the first partial region of the region to be monitored.

To ensure that smoke, which is present in a second partial region of the region to be monitored, is transported to the at least one smoke detector, a fluid stream injected into the region to be monitored by means of the fluid injection device preferably extends at least along a part of its length first through the second partial region and thereafter through the first partial region. Preferably, the fluid stream is a focused stream extending in a substantially linear direction between the fluid injection device and the smoke detector. Smoke, which is present in a second partial region of the region to be monitored, then may be entrained by the fluid stream and transported into the first partial region and hence to the at least one smoke detector. The fluid injection device may be installed in a sidewall region of the region to be monitored by means of the smoke detection system. A fluid stream exiting the fluid injection device then may flow from the sidewall region of the region to be monitored across the second partial region, which is formed by lower region of the region to be monitored, and finally enter the first partial region formed by a ceiling region of the region to be monitored.

In the smoke detection system according to the invention, the injection of fluid into the region to be monitored by means of the fluid injection device ensures that smoke which is generated or present in the second partial region of the region to be monitored is quickly transported to the smoke detector. The smoke detection system thus allows a quick and reliable detection of smoke, even if the smoke is generated at a site remote from the smoke detector. In particular, smoke which is transported to the smoke detector by the fluid stream injected into the region to be monitored by means of the fluid injection device reaches the smoke detector much faster than smoke which rises to the smoke detector from the second partial region due to thermal convection or smoke which is drawn in by an aspirating smoke detector, since the aspirating smoke detector, before being able to detect the smoke, has to draw in all the smoke-free air surrounding the smoke detector. Of course, a particularly reliable and quickly reacting smoke detection system is obtained by equipping the smoke detection system according to the invention with an aspirating smoke detector.

The smoke detection system is particularly suitable for use in a vehicle such as an aircraft which is operated at ambient conditions which may cause the formation of air layers having different temperatures and hence may hinder or delay a movement of smoke generated at a site remote from the smoke detector to the smoke detector. Specifically, the installation of additional smoke detectors with suitable electrical connections in the second partial region of the region to be monitored may be dispensed with. Further, the reduction of the number of smoke detectors which are required to reliably monitor the region to be monitored simplifies the processing of the electronic signals provided by the smoke detectors. In addition, also ventilation means for dissolving undesired air layer structures are no longer necessary. The smoke detection system according to the invention thus is particularly lightweight, easy to install and easy to operate.

Preferably, the fluid injection device is configured to inject the fluid into the region to be monitored at a speed which is adjusted to the distance between the fluid injection device and the at least one smoke detector such that a fluid stream which is injected into the region to be monitored by means of the fluid injection device impinges on the at least one smoke detector. The speed at which the fluid should be injected into the region to be monitored should increase with an increasing distance between the fluid injection device and the smoke detector.

Preferably, the fluid injection device is configured to inject a focused fluid stream extending in a substantially linear direction between the fluid injection device and the smoke detector into the region to be monitored at such a speed that the fluid stream and in particular the direction of the fluid stream is not altered by natural thermal or generated movements of the ambient air in the region to monitored. Specifically, the fluid injection device may be configured to inject the fluid stream into the region to be monitored at such a speed that the fluid stream is not deflected by ambient air swirls generated, for example, by an air conditioning system for air conditioning the region to be monitored such that the injected fluid stream still unerringly impinges on the smoke detector.

The fluid injection device may be configured to inject the fluid into the region to be monitored at a speed of approximately 20 to 30 m/s, preferably approximately 25 m/s. A fluid stream injected into the region to be monitored at that speed has a reach of approximately 3.5 to 4.5 m, preferably approximately 4 m and thus ensures that smoke generated or present in the second partial region is quickly transported to the smoke detector.

The fluid injection device may comprise a fluid supply nozzle which is oriented in the direction of the at least one smoke detector. By orienting a fluid supply nozzle in the direction of the at least one smoke detector it may be ensured that a fluid stream exiting the fluid supply nozzle is directed to smoke detector and impinges on the smoke detector.

The injection speed of the fluid injected into the region to be monitored may be adjusted by suitably selecting the flow cross-section of a fluid outlet opening of the fluid injection device. Preferably, the fluid outlet opening of the fluid injection device has a flow cross-section of approximately 200 to 300 mm$^2$, preferably approximately 250 mm$^2$.

The fluid injection device may comprise an orifice plate for stepwise or continuous variation of the flow cross-section of the fluid outlet opening of the fluid injection device. By varying the flow cross-section of the fluid outlet opening, the injection speed of the fluid stream injected into the region to be monitored may be varied as desired.

In general, the fluid injection device may be configured to inject any desired fluid, in particular any desired gas, into the region to be monitored. Preferably, however, the fluid injected into the region to be monitored by means of the fluid injection device is air. In order to supply air to the fluid injection device the fluid injection device may be connected to an air supply line of a ventilation system for ventilating the region to be monitored. Air flowing through the air supply line then may be branched off from the air supply line and, by means of the fluid injection device, injected into the region to be monitored. Additional fluid supply lines for supplying fluid to be injected into the region to be monitored by means of the fluid injection device thus can be dispensed with.

In the smoke detection system a plurality of fluid injection devices may be associated with one smoke detector. Preferably the fluid injection devices are arranged relative to the smoke detector such that the fluid streams injected into the region to be monitored by the fluid injection devices extend in different spatial directions towards the smoke detector. In particular, the fluid streams injected into the region to be monitored by the fluid injection devices may extend in at least one spatial plane non-parallel to each other, such that the fluid streams do not interfere with each other. Associating a plurality of fluid injection devices with one smoke detector provides for an increased system redundancy in case the flow path of one fluid stream should be blocked, for example by an obstacle. Further, the efficiency of the system is increased, since only one smoke detector is necessary to detect smoke transported to the smoke detector from different spatial directions.

In a preferred embodiment the smoke detection system may comprise a plurality of smoke detectors which are installed in the first partial region of the region to be monitored. A smoke detection system comprising a plurality of smoke detectors may be used for monitoring a region having a large volume such as, for example, the cabin of a vehicle, in particular an aircraft. The smoke detectors may be installed in the first partial region of the region to be monitored in the direction of an axis, preferably a longitudinal axis, of the region to be monitored. Further, the smoke detection system may comprise a plurality of fluid injection devices. Preferably, each smoke detector of the smoke detection system is associated with at least one fluid injection device. The fluid injection devices may be connected to an air supply line of a ventilation system for ventilating the region to be monitored, wherein the air supply line may extend substantially parallel to the axis of the region to be monitored. For example, fluid supply nozzles of the fluid injection devices may extend at an angle from the air supply line of the ventilation system such that a fluid stream exiting the fluid outlet opening of each fluid injection device impinges on a smoke detector associated with the fluid injection device.

A first plurality of fluid injection devices may be connected to a first air supply line of a ventilation system for ventilating the region to be monitored. The first air supply line may extend along a first sidewall of the region to be monitored. A second plurality of fluid injection devices may be connected to a second air supply line of the ventilation system for ventilating the region to be monitored. The second air supply line may extend along a second sidewall of the region to be monitored. The second sidewall may be located opposite to the first sidewall. For example, fluid supply nozzles of the first plurality of fluid injection devices may extend at an angle from the first air supply line of the ventilation system such that a fluid stream exiting the fluid outlet opening of each fluid injection device impinges on a smoke detector associated with the fluid injection device. Similarly, fluid supply nozzles of the second plurality of fluid injection devices may extend at an angle from the second air supply line of the ventilation system such that a fluid stream exiting the fluid outlet opening of each fluid injection device impinges on a smoke detector associated with the fluid injection device. In such a configuration, each smoke detector of the smoke detection system may be associated with at one fluid injection device of the first plurality of fluid injection devices and one fluid injection device of the second plurality of fluid injection devices.

In a method for operating a smoke detection system according to the invention, at least one smoke detector which is installed in the first partial region of a region to be monitored by means of the smoke detection system is provided. A fluid is injected into the region to be monitored in a direction of the at least one smoke detector such that in an emergency case, when smoke is present in a second partial region of the region to be monitored, the smoke is transported to the at least one smoke detector.

The fluid injection device may inject the fluid into the region to be monitored at a speed which is adjusted to the distance between the fluid injection device and the at least one smoke detector such that a fluid stream which is injected into said region to be monitored by means of the fluid injection device impinges on the at least one smoke detector.

The fluid injection device may inject the fluid into the region to be monitored at a speed of approximately 20 to 30 m/s, preferably approximately 25 m/s.

The fluid injection device may inject the fluid into the region to be monitored via a fluid outlet opening having a flow cross-section of approximately 200 to 300 mm$^2$; preferably approximately 250 mm$^2$.

Preferably, the flow cross-section of the fluid outlet opening of the fluid injection device is varied in a stepwise or continuous manner by means of an orifice plate.

The fluid to be injected into the region to be monitored may be supplied to the fluid injection device by an air supply line of a ventilation system for ventilating the region to be monitored.

In the method for operating a smoke detection system a plurality of fluid streams may be injected into the region to be monitored by a plurality of fluid injection devices associated with one smoke detector. The fluid streams may extend in different spatial directions towards the smoke detector. In particular, the fluid streams may extend in at least one spatial plane non-parallel to each other, such that the fluid streams do not interfere with each other.

An above described smoke detection system and/or an above described method for operating a smoke detection system is/are particularly suitably for use in a vehicle, in particular an aircraft.

BRIEF DESCRIPTION OF DRAWINGS

Preferred embodiments of the invention now are described in greater detail with reference to the appended schematic drawings, wherein FIG. 2 shows a top view of the aircraft cabin depicted in FIG. 1, and FIG. 3 shows a top view of an aircraft cabin which is equipped with an alternative embodiment of the smoke detection system according to the invention.

DETAILED DESCRIPTION OF EMBODIMENTS

Figure 1:
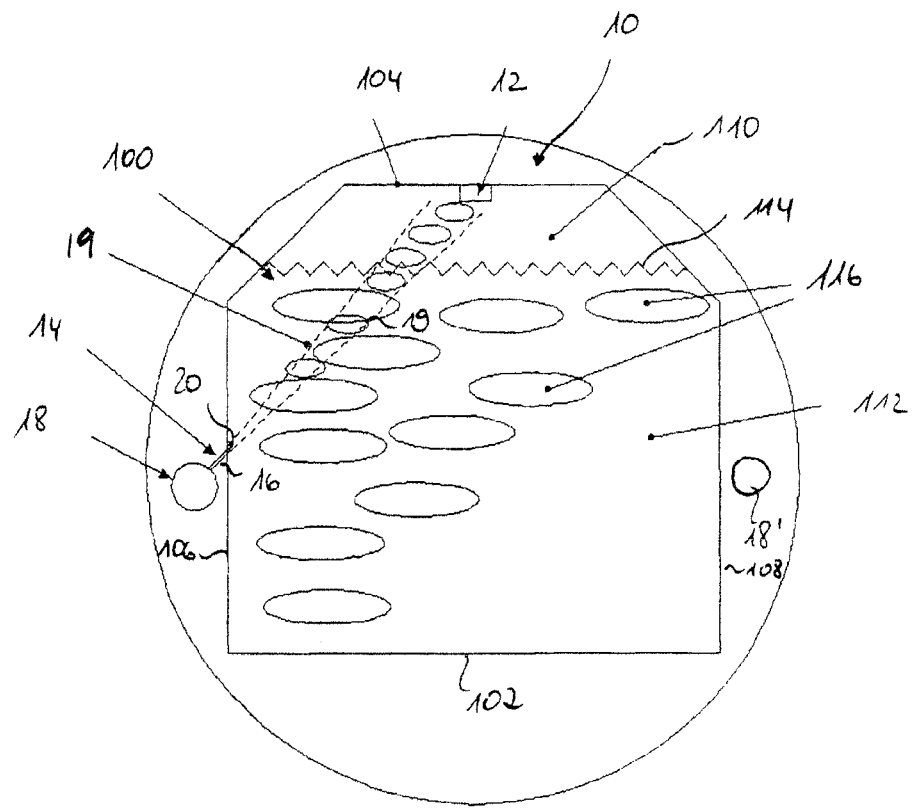
FIG. 1 shows a cross-sectional view of an aircraft cabin which is equipped with a smoke detection system according to the invention.

FIG. 1 shows a cross-sectional view of a region 100 to be monitored by a smoke detection system 10. In the arrangements according to FIG. 1 the region 100 to be monitored by the smoke detection system 10 is an aircraft cabin. The region 100 to be monitored is delimited by a floor 102, a ceiling 104, a first side wall 106 and a second side wall 108. The sidewalls 106, 108 are located opposite to each other. The smoke detection system 10 comprises a plurality of smoke detectors 12 which are installed in a first partial region 110 of the region 100 to be monitored. Specifically, the smoke detectors 12 are attached to the ceiling 104 of the region 100 to be monitored, i.e. the ceiling 104 of the aircraft cabin, wherein the smoke detectors 12 are distributed along a longitudinal axis L of the region 100 to be monitored, see FIG. 2. The first partial region 110 of the region 100 to be monitored in the arrangement according to FIG. 1 thus is formed by a ceiling region of the of the region 100 to be monitored.

When the aircraft is operated on the ground at hot ambient temperatures and/or intense solar radiation, due to heating of the aircraft outer shell, a layer of warm air forms adjacent to the ceiling 104 of the region 100 to be monitored, i.e. in the first partial region 110 of the region 100 to be monitored. Contrary thereto, in a second partial region 112 of the region 100 to be monitored, which in the arrangement according to FIG. 1 is formed by a lower region of the of the region 100 to be monitored, the supply of cool air conditioned air from an aircraft air conditioning system causes the formation of a layer of cool air.

This layer of cool air prevailing in the second partial region 112 of the region 100 to be monitored is "covered" by the layer of warm air present in the first partial region 110 of the region 100 to be monitored. An interface between the air layers in FIG. 1 is designated with the reference numeral 114. In an emergency case, when smoke 116 is generated or present in the second partial region 112 of the region 100 to be monitored, i.e. in the region of the aircraft cabin where cool air conditioned air prevails, the warm air layer "covering" the cool air layer may hinder or at least delay that the smoke 116, due to thermal convection, rises to the ceiling 104, i.e. into the first partial region 110 of the region 100 to be monitored where it can be detected by the smoke detectors 12.

The smoke detection system 10 therefore further comprises a plurality of fluid injection devices 14. Specifically, in the arrangement according to FIGS. 1 and 2 each smoke detector 12 is associated with one fluid injection device 14. Each fluid injection device 14 comprises a fluid supply nozzle 16 branching off from a first air supply line 18 of a ventilation system of the aircraft, the first air supply line 18 extending along the first sidewall 106 of the region 100 to be monitored substantially parallel to the longitudinal axis L of the region 100 to be monitored. Specifically, the fluid supply nozzle 16 of each fluid injection device 14 is oriented in the direction of a smoke detector 12 associated with the fluid injection device 14, i.e. extends at an angle from the first air supply line 18 which is selected such that a fluid stream 19 exiting the fluid outlet opening 20 of each fluid injection device 14 flows in the direction of the smoke detector 12 associated with the injection device 14. The fluid stream 19 exiting the fluid outlet opening 20 of each fluid injection device 14 is an air stream which is generated by fluid injection device 14 from the air which is supplied to the fluid injection device 14 via the first air supply line 18.

The fluid outlet opening 20 of each fluid injection device 14 has a flow cross-section of approximately 250 mm². If desired, an orifice plate (not shown in the drawings) may be provided in the fluid injection devices 14 for varying the flow cross-section of the fluid outlet openings 20 in a stepwise or continuous manner. By suitably adjusting the flow cross-section of the fluid outlet opening 20 of each fluid injection device 14, the injection speed of the fluid stream 19 injected into the region 100 to be monitored may be set to approximately 25 m/s. Hence, the fluid stream 19 injected into the region 100 to be monitored by each fluid injection device 14 bridges the distance between the fluid outlet opening 20 of the fluid injection device 14 and the smoke detector 12 associated with the fluid injection device 14 such that the fluid stream 19 exiting the air outlet opening 20 of the fluid injection device 14 impinges on the smoke detector 12 associated with the fluid injection device 14.

In an emergency case, when smoke 116 is generated or present in the second partial region 112 of the region 100 to be monitored, the smoke 116 is entrained by the fluid streams 19 injected into the region 100 to be monitored by the fluid injection device 14 and transported the smoke detectors 12. Thus, the presence of smoke 116 may be detected quickly, even in a case wherein the formation of air layers having different temperatures within the region 100 to be monitored may hinder or at least delay that the smoke 116 rises to smoke detectors 12 due to thermal convection.

In the arrangement depicted in FIG. 3 a first plurality of fluid injection devices 14 is connected to the first air supply line 18 of the ventilation system for ventilating the region 100 to be monitored and a second plurality of fluid injection devices 14 is connected to a second air supply line 18' of the ventilation system for ventilating the region 100 to be monitored. The second air supply line 18' extends along the second sidewall 108 of the region 100 to be monitored substantially parallel to the first air supply line 18 and substantially parallel to the longitudinal axis L of the region to be monitored.

The fluid supply nozzles 16 of the first plurality of fluid injection devices 16 extend at an angle from the first air supply line 18 of the ventilation system such that a fluid stream 19 exiting the fluid outlet opening 20 of each fluid injection device 14 impinges on a smoke detector 12 associated with the fluid injection device 14. Similarly, fluid supply nozzles 16 of the second plurality of fluid injection devices 14 extend at an angle from the second air supply line 18' of the ventilation system such that a fluid stream 19 exiting the fluid outlet opening 20 of each fluid injection device 16 impinges on a smoke detector 12 associated with the fluid injection device 14.

Specifically, each smoke detector 12 of the smoke detection system is associated with one fluid injection device 14 of the first plurality of fluid injection devices and one fluid injection device 14 of the second plurality of fluid injection devices. The fluid streams 19 of two fluid injection devices 14 associated with one smoke detector 12 extend in different spatial directions towards the smoke detector 12. In particular, the fluid streams 19 extend in at least one spatial plane non-parallel to each other, such that the fluid streams 19 do not interfere with each other.

Otherwise, the structure and the function of the smoke detection system 10 according to FIG. 3 correspond to the structure and the function of the arrangement according to FIGS. 1 and 2.

The invention claimed is:

1. Smoke detection system configured to monitor a region to be monitored in a vehicle cabin, comprising:
   at least one smoke detector which is installed in a vehicle cabin, and
   at least one fluid injection device disposed below and remotely from the smoke detector in a sidewall region of the vehicle cabin and configured to inject a fluid into said region to be monitored in a direction of the at least one smoke detector such that in an emergency case, when smoke is present in a region of said region to be monitored, the smoke is transported by the injected fluid to the at least one smoke detector.

2. System according to claim 1,
   wherein the fluid injection device is configured to inject the fluid into said region to be monitored at a speed which is adjusted to the distance between the fluid injection device and the at least one smoke detector such that a fluid stream which is injected into said region to be monitored by means of the fluid injection device impinges on the at least one smoke detector.

3. System according to claim 1,
   wherein the fluid injection device is configured to inject the fluid into said region to be monitored at a speed of approximately 20 to 30 m/s, preferably approximately 25 m/s.

4. System according to claim 1,
   wherein the fluid injection device comprises a fluid supply nozzle which is oriented in the direction of the at least one smoke detector and/or a fluid outlet opening having a flow cross-section of approximately 200 to 300 mm2, preferably approximately 250 mm2.

5. System according to claim 4,
   wherein the fluid injection device comprises an orifice plate for stepwise or continuous variation of the flow cross-section of the fluid outlet opening of the fluid injection device.

6. System according to claim 1,
   wherein the fluid injection device is connected to an air supply line of a ventilation system for ventilating said region to be monitored.

7. System according to claim 1,
   wherein a plurality of fluid injection devices is associated with the smoke detector, wherein the fluid injection devices are arranged relative to the smoke detector such that the fluid streams injected into said region to be monitored by the fluid injection devices extend in different spatial directions towards the smoke detector.

8. System according to claim 1,
   further comprising
   a plurality of smoke detectors which are installed in the region of said region to be monitored in the direction of an axis of said region to be monitored, and
   a plurality of fluid injection devices which are connected to an air supply line of a ventilation system for ventilating said region to be monitored, the air supply line extending substantially parallel to the axis of said region to be monitored and along the sidewall of the vehicle cabin, wherein each smoke detector is associated with at least one fluid injection device.

9. System according to claim 1,
   wherein a first plurality of fluid injection devices is connected to a first air supply line of a ventilation system for ventilating said region to be monitored, said first air supply line extending along a first sidewall of said region to be monitored, and in that a second plurality of fluid injection devices is connected to a second air supply line of the ventilation system for ventilating said region to be monitored, said second air supply line extending along a second sidewall of said region to be monitored, said second sidewall being located opposite to said first sidewall.

10. Method for monitoring a region to be monitored in a vehicle cabin using a smoke detection system, the method comprising the steps:
   providing at least one smoke detector which is installed in the vehicle cabin,
   providing a fluid injection device below and remotely from the smoke detector in a sidewall of the vehicle cabin, and
   injecting a fluid, by the fluid injection device, into said region to be monitored in a direction of the at least one smoke detector such that in an emergency case, when smoke is present in a region of said region to be monitored, the smoke is transported to the at least one smoke detector.

11. Method according to claim 10,
   wherein the fluid injection device injects the fluid into said region to be monitored at a speed which is adjusted to the distance between the fluid injection device and the at least one smoke detector such that a fluid stream which is injected into said region to be monitored by means of the fluid injection device impinges on the at least one smoke detector.

12. Method according to claim 10,
   wherein at least one fluid injection device injects the fluid into said region to be monitored at a speed of approximately 20 to 30 m/s, preferably approximately 25 m/s.

13. Method according to claim 10,
   wherein at least one fluid injection device injects the fluid into said region to be monitored via a fluid outlet opening having a flow cross-section of approximately 200 to 300 mm2, preferably approximately 250 mm2.

14. Method according to claim 13,
   wherein the flow cross-section of the fluid outlet opening of the fluid injection device is varied in a stepwise or continuous manner by means of an orifice plate.

15. Method according to claim 10,
   wherein at least one fluid to be injected into said region to be monitored is supplied to the fluid injection device by an air supply line of a ventilation system for ventilating said region to be monitored.

16. A smoke detection system for monitoring a region to be monitored in a vehicle cabin, comprising:
   a smoke detection system comprising at least one smoke detector which is installed in a ceiling region of a region to be monitored by means of the smoke detection system, and at least one fluid injection device provided in a sidewall region of the vehicle cabin and configured to inject a fluid into said region to be monitored in a direction of the at least one smoke detector such that in an emergency case, when smoke is present in a region of said region to be monitored located below the ceiling region, the smoke is transported by the injected fluid to the at least one smoke detector.

17. Method according to claim 10, wherein the step of providing at least one smoke detector includes providing in an aircraft a smoke detection system configured to monitor a region to be monitored in a vehicle cabin, the smoke detection system comprising: at least one smoke detector which is installed in the vehicle cabin, and at least one fluid injection device provided below and remotely from the smoke detector in a sidewall region of the vehicle cabin the and configured to inject a fluid into said region to be monitored in a direction of the at least one smoke detector such that in an emergency case, when smoke is present in a part of said region to be monitored, the smoke is transported by the injected fluid to the at least one smoke detector.

18. Method according to claim 10, wherein the step of providing at least one smoke detector includes providing in an aircraft a smoke detection system configured to monitor a region to be monitored in a vehicle cabin, the smoke detection system comprising:
   at least one smoke detector which is installed in the vehicle cabin, and
   at least one fluid injection device provided below and remotely from the smoke detector in a sidewall region of the vehicle cabin the and configured to inject a fluid into said region to be monitored in a direction of the at least one smoke detector such that in an emergency case, when smoke is present in a part of said region to be monitored, the smoke is transported to the at least one smoke detector,
   wherein a first plurality of fluid injection devices is connected to a first air supply line of a ventilation system for ventilating said region to be monitored, said first air supply line extending along a first sidewall of said region to be monitored, and in that a second plurality of fluid injection devices is connected to a second air supply line of the ventilation system for ventilating said region to be monitored, said second air supply line extending along a second sidewall of said region to be monitored, said second sidewall being located opposite to said first sidewall.

* * * * *